US012569567B2

(12) United States Patent
Tang et al.

(10) Patent No.: US 12,569,567 B2
(45) Date of Patent: Mar. 10, 2026

(54) RETINOIC ACID MODIFIED LYSOSOME TARGETING CHIMERA MOLECULE, PREPARATION METHOD AND APPLICATIONS THEREOF

(71) Applicant: THE FOURTH AFFILIATED HOSPITAL OF ZHEJIANG UNIVERSITY SCHOOL OF MEDICINE, Yiwu (CN)

(72) Inventors: Longguang Tang, Yiwu (CN); Kesong Peng, Yiwu (CN); Xiaoli Sun, Yiwu (CN); Songmin Ying, Yiwu (CN); Zhen Gu, Yiwu (CN); Chaoran Ji, Yiwu (CN)

(73) Assignee: THE FOURTH AFFILIATED HOSPITAL OF ZHEJIANG UNIVERSITY SCHOOL OF MEDICINE, Yiwu (CN)

( * ) Notice: Subject to any disclaimer, the term of this patent is extended or adjusted under 35 U.S.C. 154(b) by 740 days.

(21) Appl. No.: 17/946,791

(22) Filed: Sep. 16, 2022

(65) Prior Publication Data

US 2023/0241239 A1 Aug. 3, 2023

Related U.S. Application Data

(63) Continuation of application No. PCT/CN2022/113868, filed on Aug. 22, 2022.

(30) Foreign Application Priority Data

Jan. 28, 2022 (CN) ......................... 202210104646.9

(51) Int. Cl.
*A61K 47/68* (2017.01)

(52) U.S. Cl.
CPC ...... *A61K 47/6849* (2017.08); *A61K 47/6801* (2017.08)

(58) Field of Classification Search
None
See application file for complete search history.

(56) References Cited

U.S. PATENT DOCUMENTS 11,787,865 B2 * 10/2023 Bertozzi ............ A61K 47/6873 424/136.1

FOREIGN PATENT DOCUMENTS

WO WO-03037385 A1 * 5/2003 .............. A61P 11/00
WO WO-2020240041 A1 * 12/2020 ............ G01N 33/53

* cited by examiner

*Primary Examiner* — Phuong Huynh
(74) *Attorney, Agent, or Firm* — Hemisphere Law, PLLC

(57) ABSTRACT

A retinoic acid modified lysosome targeting chimera (LYTAC) molecule, a preparation method and applications thereof are provided. A structural formula of the retinoic acid modified LYTAC molecule is

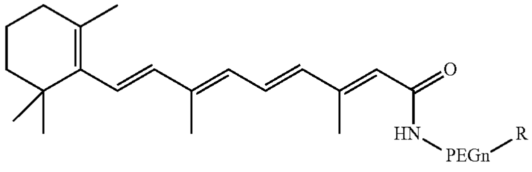

in which, n represents a molecular weight of polyethylene glycol (PEG), n is in a range of 60 to 5000, R is one of an antibody, a polypeptide and a micromolecule compound targeting a targeted protein. The retinoic acid modified LYTAC molecule can be applied to targeted protein degradation and preparation of tumor cell activity inhibitors. Retinoic acid has high biosafety, is easy to obtain and modify, and has a broad application prospect.

7 Claims, 3 Drawing Sheets

RETINOIC ACID MODIFIED LYSOSOME TARGETING CHIMERA MOLECULE, PREPARATION METHOD AND APPLICATIONS THEREOF

TECHNICAL FIELD

The disclosure relates to the field of targeted protein degradation (TPD) technologies, particular to a retinoic acid modified lysosome targeting chimera (LYTAC) molecule, a preparation method and applications thereof.

BACKGROUND

TPD induces consumption or reduction of pathogenic proteins by hijacking an endogenous protein degradation mechanism. Different from a "occupancy-driven" mode of traditional inhibitors, TPD only needs binding agents to recruit targeted proteins for degradation, and does not rely on high affinity occupation. Therefore, it can target "non-pharmaceutical" proteins that have no enzyme activity or lack available drug binding pockets. At the same time, due to its catalytic action mode, TPD technology can achieve efficient and rapid target protein consumption at a low drug concentration (i.e., nmol/L (nM) level), prolong drug action time, and avoid off-target effects and adverse reactions of the traditional inhibitors from the source.

At present, the most mature technology in TPD is proteolysis-targeting chimera (PROTAC) technology based on ubiquitination-protease system for degradation of intracellular proteins. ARV-110, a first androgen receptor targeting degradation agent developed based on this technology, has completed phase I clinical trials (NCT03888612), showing good efficacy and safety in patients with metastatic castration resistant prostate cancer. At present, many well-known pharmaceutical companies at home and abroad, such as Arvinas and Novartis, have deployed the PROTAC technology, which shows the broad market potential of this technology.

As a supplement to PROTAC, in 2020, Carolyn Bertozzi and others proposed a lysosome-targeting chimeras (LYTAC) technology, which used an endocytosis-lysosome pathway for the first time to realize the targeted degradation of extracellular proteins and membrane proteins through targeting the extracellular domains of proteins. Currently reported LYTAC is mainly composed of two binding domains, one of an oligosaccharide structure of lysosome-targeting receptor (shorted as LTR), such as cation independent mannose-6-phosphate receptor (shorted as CI-M6PR), which targets cell surfaces, and the other is an antibody, a polypeptide or a micromolecule that targets targeted proteins.

After LYTAC binds with CI-M6PR and the targeted protein, the mannose-6-phosphate (shorted as M6P) modified protein is transferred to lysosome, which is reported to achieve the successful degradation of epidermal growth factor receptor (shorted as EGFR), human epidermal growth factor receptor 2 (shorted as HER2), programmed cell death 1 ligand 1 (shorted as PD-L1) and apolipoprotein E4 (shorted as apoE4), and the dissociated CI-M6PR can enter the cycle again.

However, the above LYTAC degradation agents have the following shortcomings. 1. At present, synthesis routes of LYTAC ligand poly (M6Pn) for CI-M6PR are complex, with more than 15 chemical reactions, which is difficult to be popularized and applied. 2. Nonspecific glycosyl modified antibodies will be cleared quickly in mice, so how to adjust pharmacokinetic characteristics of LYTAC to control the off-target clearance rate of LYTAC is another difficulty faced by this technology. 3. At present, the LTR ligand of LYTACs molecule is a chemically synthesized non-natural structure of saccharides, so it may produce strong immunogenicity in human body. Therefore, it is urgent to develop a new LTR ligand that is easy to obtain and has high biocompatibility.

Retinoic acid (shorted as RA) is a metabolic intermediate of vitamin A in the body, which mainly affects the growth of bone and promotes epithelial cell proliferation, differentiation, keratinolysis and other metabolic effects. It has been reported that the retinoic acid can also be used as a ligand for CI-M6PR. However, it has not been reported that retinoic acid coupled antibodies or peptides are used as LYTAC drugs to degrade membrane proteins. Because the retinoic acid has high biosafety and the carboxyl group in its structure is easy to modify and couple with other drugs, the disclosure attempts to couple it with the antibody, the peptide or the micromolecular compound to realize the degradation of membrane receptor proteins.

SUMMARY

The disclosure provides a retinoic acid modified LYTAC molecule, a preparation method and applications thereof, a retinoic acid targets an antibody, a peptide or a micromolecule compound of a targeted protein by chemical coupling to prepare a targeted drug, which can be applied to a new targeted protein degradation technology—LYTAC technology.

The technical schemes of the disclosure are as follows.

A retinoic acid modified LYTAC molecule, and a structural formula of the retinoic acid modified LYTAC molecule is shown as following Formula I:

(Formula I)

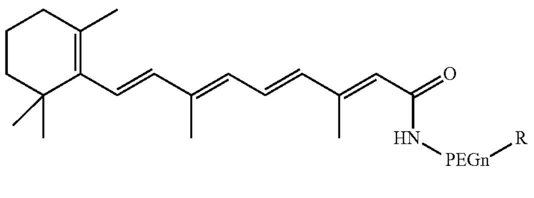

where n represents a molecular weight of polyethylene glycol (PEG), n is in a range of 60 to 5000, and R is one of an antibody, a polypeptide and a micromolecule compound targeting a targeted protein.

A molecular formula of the retinoic acid is $C_{20}H_{28}O_2$, it is a metabolic intermediate of vitamin A in the body, it has high biosafety, is easy to obtain and is easy to modify. By coupling the retinoic acid with any antibody, polypeptide or micromolecule compound targeting the targeted protein, the retinoic acid modified LYTAC molecule can be obtained, which can realize the degradation of the targeted protein.

Preferably, the n is in a range of 120 to 3000.

Preferably, the R is one selected from a group consisting of antibodies or polypeptides of membrane proteins, and antibodies or polypeptides of extracellular proteins, such as the R is one selected from the group consisting of anti-epidermal growth factor receptor (anti-EGFR) antibody cetuximab, anti-programmed cell death 1 ligand 1 (anti-PDL-1) antibody atezolizumab, EGFR-blinding polypeptide GE11, anti-human epidermal growthfactor receptor 2 (anti-HER2) antibody HERCEPTIN, anti-G protein-coupled receptor (anti-GPCR) related antibody, anti-fibroblast growth factor receptor (anti-FGFR) antibody, anti-vascular endothelial growth factor receptor (anti-VEGFR) antibody, anti-cytotoxic t-lymphocyte-associated protein 4 (anti-CTLA4) antibody and anti-interleukin-5 receptor α-subunit (anti-IL-5Rα) antibody.

The disclosure further provides a preparation method of the retinoic acid modified LYTAC molecule, including:

(1), reacting a retinoic acid with $NH_2$-$PEG_n$-Mal, and then obtaining an intermediate after separation and purification;

(2), reacting the intermediate with the one of the antibody, the polypeptide and the micromolecule compound with a sulfhydryl group targeting the targeted protein, and then obtaining the retinoic acid modified LYTAC molecule after a first post-treatment.

Preferably, the step (1) includes: dissolving the RA into a solvent, and then adding 1-ethyl-(3-dimethylaminopropyl)-3-ethylcarbodiimide hydrochloride (EDC·HCL) and N-hydroxysuccinimide (NHS) to perform an ice bath reaction for 30 minutes (min) to 60 min to obtain an initial reaction mixture; adding $NH_2$-$PEG_n$-Mal into the initial reaction mixture for reaction at room temperature for 10 hours (h) to 15 h to obtain a reaction mixture, and performing a second post-treatment on the reaction mixture to obtain the intermediate.

In the step (1), the second post-treatment includes: removing the solvent in the reaction mixture to obtain an oily concentrate; dissolving the oily concentrate in a mixed solvent of ultra-pure water and methanol with a volume ratio of 4:1, and then performing the separation and the purification by using preparative high performance liquid chromatography;

a model of a chromatographic column is COSMOSIL 5C18-MS-II 20 mm*250 mm; a mobile phase is a mixed solvent of ultra-pure water and methanol with a volume ratio of 3:7; an elution rate is 4 mL/min; a column temperature is 30° C.; and a retention time is 14 min.

Preferably, in the step (1), a molar ratio of the retinoic acid to the $NH_2$-$PEG_n$-Mal is 1:0.5 to 2; and the most preferred ratio is 1:1.

Preferably, the step (2) includes: dissolving the intermediate and the one of the antibody, the polypeptide and the micromolecule compound with the sulfhydryl group targeting the targeted protein in a phosphate buffered saline (PBS) buffer for reaction at room temperature for 1 h to 5 h, removing unreacted raw materials after the reaction, and then drying to obtain the retinoic acid modified LYTAC molecule.

Preferably, in the step (2), a molar ratio of the intermediate to the one of the antibody, the polypeptide and the micromolecule compound with the sulfhydryl group targeting the targeted protein is 8 to 10:1; and the most preferred ratio is 10:1.

The retinoic acid modified LYTAC molecule of the disclosure has strong targeted protein degradation and can be used as a targeted protein degradation agent.

The disclosure further provides a method of an application of the retinoic acid modified LYTAC molecule in targeted protein degradation, includes: performing targeted degradation on a membrane protein or an extracellular protein such as EGFR, PDL-1 or HER2 protein.

The disclosure further provides a method of an application of the retinoic acid modified LYTAC molecule in preparing an activity inhibitor of a tumor cell.

The tumor cell includes breast cancer cells, oral cancer cells, liver cancer cells, lung cancer cells, gastric cancer cells, pancreatic cancer cells, colorectal cancer cells, bladder cancer cells or prostate cancer cells and other tumor cells.

Compared with the prior art, the beneficial effects of the disclosure are as follows.

The disclosure provides a retinoic acid modified LYTAC molecule with simple structure and easy preparation, which can be used as a targeted protein degradation agent. The retinoic acid has high biosafety, is easy to obtain, and is easy to modify, it can be coupled with any antibody, polypeptide or micromolecule that targets the binding protein receptor to realize the lysosomal degradation of extracellular or membrane proteins, it can be used in the preparation of anti-tumor drugs, the treatment of inflammatory related diseases, the treatment of neurodegenerative diseases and other related diseases caused by the high expression of membrane proteins or extracellular proteins, and it has a broad application prospect.

DETAILED DESCRIPTION OF EMBODIMENTS

The disclosure is further described below in combination with specific embodiments, but the scope of protection of the disclosure is not limited to this.

The room temperature of the disclosure is in a range of 25° C. to 30° C.

Embodiment 1: Synthesis of an Intermediate RA-PEG2K-Mal

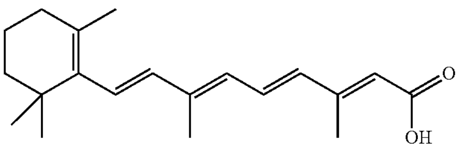

+

Retinotic acid. RA

-continued

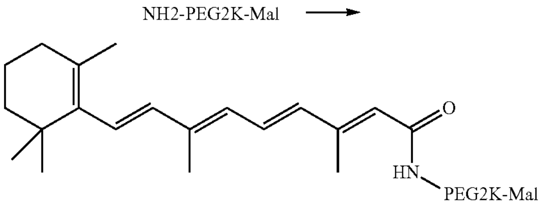

RA-PEG2K-Mal

Adding the retinoic acid (10.2 mg, 34 μmol) to dichloromethane (shorted as DCM) to dissolve, then adding 1-(3-Dimethylaminopropyl)-3-ethylcarbodiimide hydrochloride (shorted as EDC·HCL) (17.1 mg, 90 μmol) and N-Hydroxysuccinimide (shorted as NHS) (10.3 mg, 90 μmol) to perform an ice bath reaction for half an hour to obtain an initial reaction mixture, and adding NH2-PEG2K-Mal (MW: 2000) (34 μmol, 68 mg) to the initial reaction mixture for reaction at room temperature for 12 h to obtain a reaction mixture, rotating and evaporating the reaction mixture to remove dichloromethane to obtain an oily concentrate; after the oily concentrate is dissolved in a mixed solvent of ultra-pure water and methanol with a volume ratio of 4:1, performing separation and purification by using preparative high performance liquid chromatography (a model of a chromatographic column is COSMOSIL 5C18-MS-II 20 mm*250 mm), and eluting with a mixed solvent of ultra-pure water and methanol with a volume ratio of 3:7 as a mobile phase, an elution rate is 4 mL/min, a detection wavelength is 254 nm, a column temperature is 30° C., and a retention time is 14 min, a product RA-PEG2K-Mal is collected, after rotating and evaporating the methanol, freeze-drying was performed to obtain the intermediate RA-PEG2K-Mal with 0.071 g.

Embodiment 2: Synthesis of RA-PEG2K-Ctx, a Product of the Retinoic Acid Coupled with Anti-EGFR Antibody Cetuximab

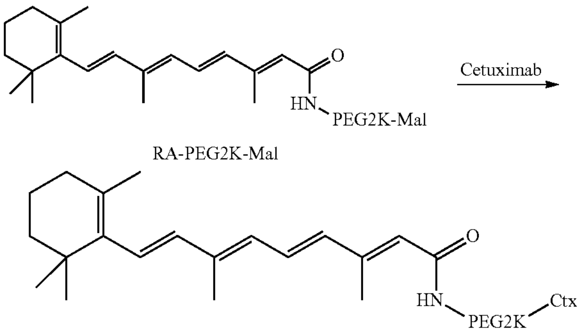

RA-PEG2K-Ctx

Figure 1:
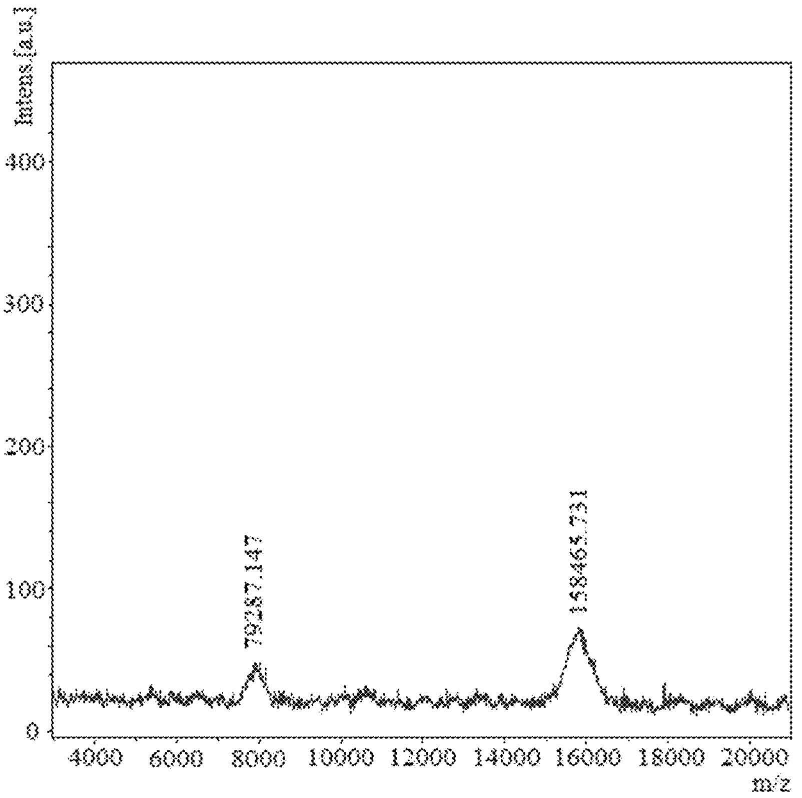
FIG. 1 shows mass spectrum test results of RA-PEG2K-Ctx, a product of retinoic acid coupled with anti-EGFR antibody cetuximab prepared in an embodiment 2.

Incubating the anti-EGFR antibody cetuximab (14.5 mg, 0.1 μmol) with tris (2-carboxyethyl) phosphine hydrochloride (shorted as TCEP) (0.28 mg, 1 μmol) in 2 ml phosphate buffered saline (PBS) buffer for half an hour, then adding the intermediate RA-PEG2K-Mal (2.4 mg, 1 μmol) prepared by the embodiment 1 into the above solution for reaction at room temperature for 3 h, after the reaction, unreacted raw materials were removed by centrifugation with an ultrafiltration centrifuge tube (MWCO 50 KD). After freeze-drying, 10.2 mg of LYTAC drug (recorded as RA-PEG2K-Ctx) shown as Formula I was obtained. The mass spectrum is shown in FIG. 1. A molecular weight of cetuximab (shorted as Ctx) is 145779.44, and a molecular weight of the product RA-PEG2K-Ctx is 158465.73, so each antibody is connected with 5 molecules of the retinoic acid.

(Formula I)

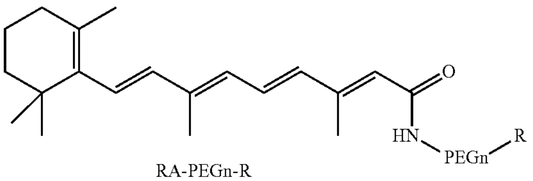

RA-PEGn-R
R= antibody, polypeptide, small molecule n= 60-5000

Embodiment 3: Synthesis of RA-PEG2K-Ate, a Product of the Retinoic Acid Coupled with Anti-PDL-1 Antibody Atezolizumab

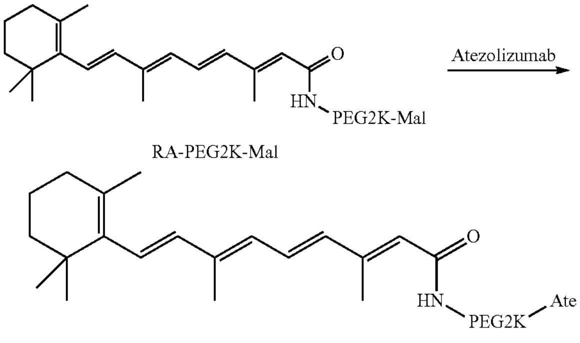

RA-PEG2K-Ate

Figure 2:
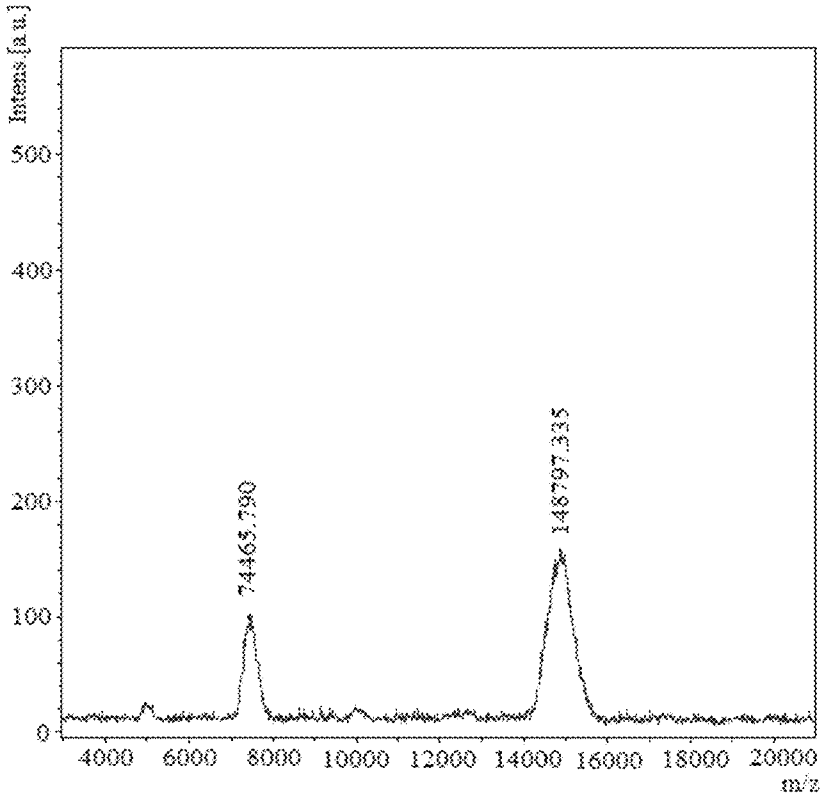
FIG. 2 shows mass spectrum test results of RA-PEG2K-Ate, a product of retinoic acid coupled with anti-PDL-1 antibody atezolizumab prepared in an embodiment 3.

Incubating anti-PDL-1 antibody atezolizumab (14.4 mg, 0.1 μmol) with TCEP (0.28 mg, 1 μmol) in 2 ml PBS buffer for half an hour, then adding the intermediate RA-PEG2K-Mal (2.4 mg, 1 μmol) prepared by the embodiment 1 into the above solution for reaction at room temperature for 3 h, after the reaction, unreacted raw materials were removed by centrifugation with an ultrafiltration centrifuge tube (MWCO 50 KD). After freeze-drying, 10.1 mg of a LYTAC drug (recorded as RA-PEG2K-Ate) shown as Formula I was obtained. The mass spectrum is shown in FIG. 2. A molecular weight of atezolizumab (shorted as Ate) is 144590.5, and a molecular weight of the product RA-PEG2K-Ate is 148797.335, so each antibody is connected with 2 molecules of the retinoic acid.

Embodiment 4: Evaluations of Degradation Effects of RA-PEG2K-Ctx on EGFR Proteins of Two Tumor Cells (after 24 Hours of Incubation)

Figure 3A:
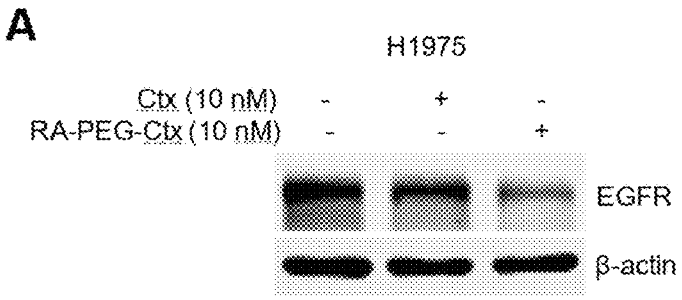
FIG. 3A shows an evaluation of a degradation effect of RA-PEG2K-Ctx on an EGFR receptor protein of a lung cancer cell H1975 (after incubation for 24 hours) in an embodiment 4.
Figure 3B:
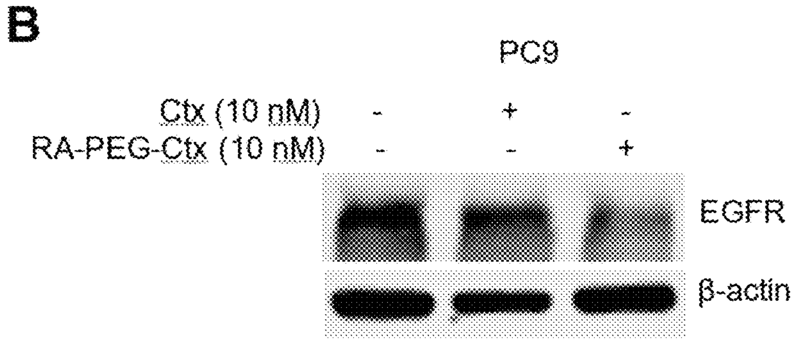
FIG. 3B shows an evaluation of a degradation effect of RA-PEG2K-Ctx on the EGFR receptor protein of a lung cancer cell PC9 (after incubation for 24 hours) in the embodiment 4.

Anti-EGFR antibody cetuximab (10 nM) and RA-PEG2K-Ctx (10 nM) are respectively added into the tumor cells: H1975 cells and PC9 cells. After incubation for 24 hours, the proteins were collected and the expressions of EGFR were detected by western blot (shorted as WB). The results are shown in FIG. 3A and FIG. 3B. EGFR proteins were expressed in both blank group and Ctx treatment group. Compared with the blank group, the EGFR protein in the RA-PEG-Ctx treatment group was degraded by more than 50%. The results showed that the RA-PEG-Ctx has a good degradation effect on the EGFR proteins of the two tumor cells.

Embodiment 5: Evaluations of Degradation Effects of RA-PEG2K-Ctx on EGFR Proteins of Two Tumor Cells (After 48 Hours of Incubation)

Figure 4A:
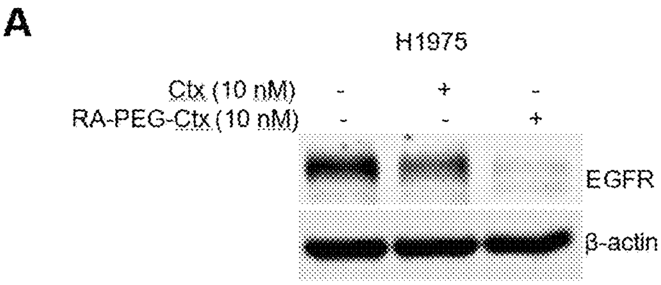
FIG. 4A shows an evaluation of a degradation effect of RA-PEG2K-Ctx on an EGFR receptor protein of a lung cancer cell H1975 (after incubation for 48 hours) in an embodiment 5.
Figure 4B:
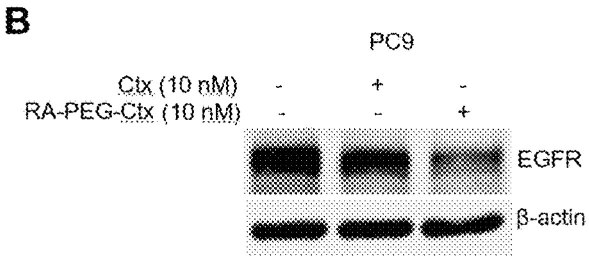
FIG. 4B shows an evaluation of a degradation effect of RA-PEG2K-Ctx on the EGFR receptor protein of a lung cancer cell PC9 (after incubation for 48 hours) in the embodiment 5.

Anti-EGFR antibody cetuximab (10 nM) and RA-PEG2K-Ctx (10 nM) are respectively added into the tumor cells: H1975 cells and PC9 cells. After incubation for 48 hours, the proteins were collected and the expressions of EGFR were detected by WB. The results are shown in FIG. 4A and FIG. 4B. EGFR proteins were expressed in both blank group and Ctx treatment group. Compared with the blank group, the EGFR protein in the RA-PEG-Ctx treatment group was degraded by more than 80%. The results showed that the RA-PEG-Ctx has a good degradation effect on the EGFR proteins of the two tumor cells.

Embodiment 6: Evaluation of a Degradation Effect of RA-PEG2K-Ate on PDL-1 Protein of a Tumor Cell MDA-MB-231 (After 24 hours of Incubation)

Figure 5:
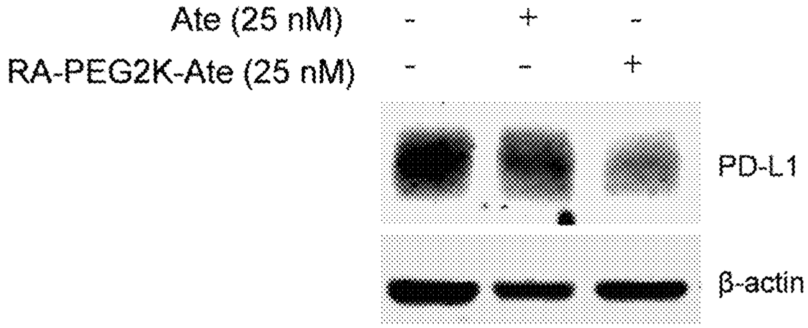
FIG. 5 shows an evaluation of a degradation effect of RA-PEG2K-Ate on a PDL-1 protein of a tumor cell MDA-MB-231 (after incubation for 24 hours) in an embodiment 6.

Anti-PDL-1 antibody atezolizumab (Ate) (25 nM) and RA-PEG2K-Ate (25 nM) were added to breast cancer cells, i.e., MDA-MB-231 cells respectively. After incubation for 24 hours, the proteins were collected and the expression of PDL-1 were detected by WB. The results are shown in FIG. 5. The expressions of the PDL-1 proteins in the blank group and the Ate treatment group are basically the same. Compared with the blank group, the PDL-1 protein in the RA-PEG-Ate treatment group was degraded by more than 50%. The results showed that the RA-PEG2K-Ate has a good degradation effect on the PDL-1 protein.

The above-mentioned embodiments have described in detail the technical schemes and beneficial effects of the disclosure. It should be understood that the above-mentioned embodiments are only specific embodiments of the disclosure and are not used to limit the disclosure. Any amendments, supplements and equivalent replacements made within the scope of the principles of the disclosure should be included in the scope of protection of the disclosure.

What is claimed is:

1. A preparation method of a retinoic acid (RA) modified lysosome targeting chimera (LYTAC) molecule, comprising:

reacting the RA with amino-(polyethylene glycol)$_n$-maleimide ($NH_2$-PEG$_n$-Mal), and then obtaining an intermediate after separation and purification; and reacting the intermediate with anti-epidermal growth factor receptor (anti-EGFR) antibody cetuximab, and then obtaining the RA modified LYTAC molecule after a first post-treatment;

wherein a structural formula of the RA modified LYTAC molecule is shown as following Formula I:

(Formula I)

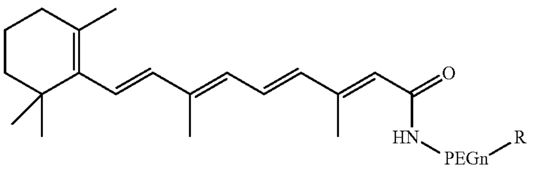

where n=2000, R is the anti-EGFR antibody cetuximab; and wherein a molar ratio of the intermediate to the anti-EGFR antibody cetuximab is 8 to 10:1.

2. The preparation method according to claim 1, wherein the reacting the RA with $NH_2$-PEG$_n$-Mal, and then obtaining an intermediate after separation and purification, comprises:

dissolving the RA into a solvent, and then adding 1-ethyl-(3-dimethylaminopropyl)-3-ethylcarbodiimide hydrochloride (EDC·HCL) and N-hydroxysuccinimide (NHS) to perform an ice bath reaction for 30 minutes (min) to 60 min to obtain an initial reaction mixture; adding the $NH_2$-PEG$_n$-Mal into the initial reaction mixture for reaction at room temperature for 10 hours (h) to 15 h to obtain a reaction mixture, and performing a second post-treatment on the reaction mixture to obtain the intermediate.

3. The preparation method according to claim 2, wherein the second post-treatment comprises:

removing the solvent in the reaction mixture to obtain an oily concentrate; dissolving the oily concentrate in a mixed solvent of ultra-pure water and methanol with a volume ratio of 4:1, and then performing the separation and the purification by using preparative high performance liquid chromatography;

wherein a mobile phase is a mixed solvent of ultra-pure water and methanol with a volume ratio of 3:7; an elution rate is 4 mL/min; a column temperature is 30° C.; and a retention time is 14 min.

4. The preparation method according to claim 1, wherein a molar ratio of the RA to the $NH_2$-PEG$_n$-Mal is 1:0.5 to 2.

5. The preparation method according to claim 1, wherein the reacting the intermediate with anti-EGFR antibody cetuximab, and then obtaining the RA modified LYTAC molecule after a first post-treatment, comprises:

dissolving the intermediate and the anti-EGFR antibody cetuximab in a phosphate buffered saline (PBS) buffer for reaction at room temperature for 1 h to 5 h, removing unreacted raw materials after the reaction, and then drying to obtain the RA modified LYTAC molecule.

6. A preparation method of an RA modified LYTAC molecule, comprising:

reacting the RA with $NH_2$-PEG$_n$-Mal, and then obtaining an intermediate after separation and purification; and reacting the intermediate with anti-EGFR antibody cetuximab, and then obtaining the RA modified LYTAC molecule after a first post-treatment;

wherein a structural formula of the RA modified LYTAC molecule is shown as following Formula I:

(Formula I)

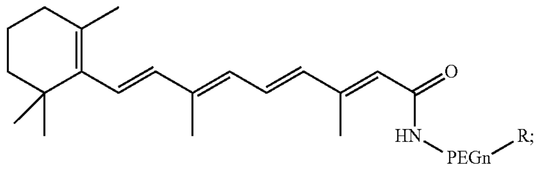

where n=2000, R is the anti-EGFR antibody cetuximab;

wherein the reacting the intermediate with anti-EGFR antibody cetuximab, and then obtaining the RA modified LYTAC molecule after a first post-treatment, comprises:

dissolving the intermediate and the anti-EGFR antibody cetuximab in a PBS buffer for reaction at room temperature for 1 h to 5 h, removing unreacted raw materials after the reaction, and then drying to obtain the RA modified LYTAC molecule.

7. A preparation method of an RA modified LYTAC molecule, comprising:

reacting the RA with $NH_2$-$PEG_n$-Mal, and then obtaining an intermediate after separation and purification; and reacting the intermediate with anti-EGFR antibody cetuximab, and then obtaining the RA modified LYTAC molecule after a first post-treatment;

wherein a structural formula of the RA modified LYTAC molecule is shown as following Formula I:

(Formula I)

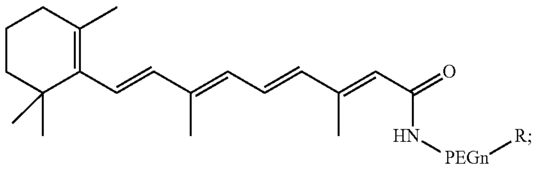

where n=2000, R is the anti-EGFR antibody cetuximab;

wherein the reacting the RA with $NH_2$-$PEG_n$-Mal, and then obtaining an intermediate after separation and purification, comprises:

dissolving the RA into a solvent, and then adding EDC·HCL and NHS to perform an ice bath reaction for 30 min to 60 min to obtain an initial reaction mixture; adding the $NH_2$-$PEG_n$-Mal into the initial reaction mixture for reaction at room temperature for 10 h to 15 h to obtain a reaction mixture, and performing a second post-treatment on the reaction mixture to obtain the intermediate;

wherein the second post-treatment comprises:

removing the solvent in the reaction mixture to obtain an oily concentrate; dissolving the oily concentrate in a mixed solvent of ultra-pure water and methanol with a volume ratio of 4:1, and then performing the separation and the purification by using preparative high performance liquid chromatography;

wherein a mobile phase is a mixed solvent of ultra-pure water and methanol with a volume ratio of 3:7; an elution rate is 4 mL/min; a column temperature is 30° C.; and a retention time is 14 min.

* * * * *